United States Patent
Engelbreth et al.

(10) Patent No.: US 10,907,674 B1
(45) Date of Patent: Feb. 2, 2021

(54) ELASTOMERIC COMPONENT AND APPARATUS AND METHOD FOR ASSEMBLY THEREOF

(71) Applicants: Daniel Engelbreth, London (CA); Noel Gulka, London (CA)

(72) Inventors: Daniel Engelbreth, London (CA); Noel Gulka, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 730 days.

(21) Appl. No.: 15/596,300

(22) Filed: May 16, 2017

Related U.S. Application Data (60) Provisional application No. 62/336,979, filed on May 16, 2016.

(51) Int. Cl.
*F16B 5/12* (2006.01)
*F16B 21/08* (2006.01)

(52) U.S. Cl.
CPC ............ *F16B 5/126* (2013.01); *F16B 21/086* (2013.01)

(58) Field of Classification Search
CPC ............................... F16B 5/126; F16B 21/086
See application file for complete search history.

(56) References Cited

U.S. PATENT DOCUMENTS

| | | | |
|---|---|---|---|
| 3,232,304 A | 2/1966 | Koester | |
| 3,295,547 A * | 1/1967 | Scaramucci | F16K 15/144 137/315.33 |
| 3,519,012 A | 7/1970 | Van Patten | |
| 3,942,547 A | 3/1976 | Pfitzner | |
| 4,057,886 A * | 11/1977 | Brass | A63H 33/12 29/235 |
| 4,456,016 A | 6/1984 | Nowacki et al. | |
| 4,709,841 A * | 12/1987 | Wollar | B21J 15/041 227/10 |
| 5,645,049 A | 7/1997 | Foley et al. | |
| 5,881,718 A | 3/1999 | Mortensen et al. | |
| 6,412,514 B1 | 7/2002 | Raftis | |
| 6,513,519 B2 | 2/2003 | Gallem | |

(Continued)

FOREIGN PATENT DOCUMENTS

| | | |
|---|---|---|
| EP | 0626180 A1 | 11/1994 |
| GB | 2333236 A | 7/1999 |

(Continued)

*Primary Examiner* — Jessica Cahill
*Assistant Examiner* — Patrick C Williams
(74) *Attorney, Agent, or Firm* — Brinks Gilson & Lione (57) ABSTRACT

An elastomeric component includes a body feature and a retaining feature coupled to the body feature. The retaining feature includes an insertion end portion, and a retention end portion spaced apart from the insertion end portion along a longitudinal axis. The insertion end portion defines a catch spaced apart from the retention end portion and having a contact location adapted to make first contact with an edge of a retaining hole. The contact location is spaced apart from the catch a first distance. The retaining feature has a blind pocket extending from the retention end portion interiorly of the retaining feature along the longitudinal axis. The blind pocket terminates at an end location spaced from the catch. The elastomeric component may be coupled to a wall defining the retaining hole. Methods of assembly, and an apparatus for installation, are also provided.

15 Claims, 6 Drawing Sheets

(56) References Cited

U.S. PATENT DOCUMENTS

| | | | |
|---|---|---|---|
| 2008/0199275 A1* | 8/2008 | Brown | F16B 13/002 411/340 |
| 2012/0138171 A1* | 6/2012 | Coolens | F01M 13/04 137/511 |
| 2014/0150790 A1 | 6/2014 | Meyer et al. | |

FOREIGN PATENT DOCUMENTS

| WO | WO2003/053500 A1 | 7/2003 |
|---|---|---|
| WO | WO2014140600 A1 | 9/2014 |

\* cited by examiner

ELASTOMERIC COMPONENT AND APPARATUS AND METHOD FOR ASSEMBLY THEREOF

This application claims the benefit of U.S. Provisional Application No. 62/336,979, filed May 16, 2016 and entitled "Elastomeric Component and Apparatus and Method for Assembly Thereof," the entire disclosure of which is hereby incorporated herein by reference.

TECHNICAL FIELD

The present invention relates generally to an elastomeric component, including for example an elastomeric valve, capable of being installed on a body by way of a push through force, as well as to an apparatus and methods for the assembly thereof.

BACKGROUND

In various manufacturing situations, it is often necessary to mechanically attach an elastomeric component, for example and without limitation a valve (flap or diaphragm), diaphragm, grommet, etc., to a rigid wall portion of another component. Often, a retaining feature of the elastomeric component will be inserted through a retaining hole. The retaining feature may have a tapered insertion feature, which typically has a retaining geometry larger than the retaining hole. The insertion feature may be pushed or pulled through the hole.

For example, the insertion feature may have a slender leading tag, which may be passed through the hole and grasped, whereinafter it may be pulled such that the insertion feature follows until the larger retaining geometry passes through the hole. Conversely, if an attempt is made to push the insertion feature through the hole, the pushing force may cause the retaining geometry to expand, and thereby resist insertion through the hole. As more force is applied, the more the component may compress and thicken at the entrance of the hole, making it increasingly difficult for insertion of the insertion feature through the hole. Accordingly, it typically is more desirable to apply a pulling force to the insertion feature rather than a pushing force.

For non-automated assembly, such pulling requires an operator to position the leading tag through the hole, grab the leading tag (with fingers or clamping tool) from the other side, and pull the insertion feature through the hole. Often, the components may be small, or the hole may be inaccessible, making the installation awkward or uncomfortable and/or time consuming. The process may also lead to repetitive strain injuries.

For a semi-automated assembly process, tools (e.g., pneumatic) may be used to align the leading tag, push the tag through the hole, grip the tag, pull the tag and insertion feature through the opening, and then release the component and tag, all of which require access to both sides of the wall and at least two tool components (pushing and pulling).

In either scenario, the leading tag may be visible or accessible on the opposite side of the wall, where the tag may be visually unattractive and/or prone to tampering. If desired, additional steps are required to remove and/or trim the tag.

SUMMARY

In one aspect, one embodiment of an elastomeric component includes a body feature and a retaining feature coupled to the body feature. The retaining feature includes an insertion end portion, and a retention end portion spaced apart from the insertion end portion along a longitudinal axis. The insertion end portion defines a catch spaced apart from the retention end portion and has a contact location adapted to make first contact with an edge of a retaining hole. The contact location is spaced apart from the catch a first distance. The retaining feature has a blind pocket extending from the retention end portion interiorly of the retaining feature along the longitudinal axis. The blind pocket terminates at an end location spaced from the catch a second distance, wherein the second distance is greater than the first distance.

In another aspect, an assembly includes a wall having first and second sides and a retaining hole extending through the wall between the first and second sides. The retaining hole has first and second edges proximate the first and second sides respectively. The insertion end portion is moveable through the retaining hole from the first side to the second side between an insertion position and a retained position. The catch engages the second side of the wall when the insertion end portion is moved to the retained position. The contact location makes a first contact with the first edge of the retaining hole when the insertion end portion is in the insertion position.

In yet another aspect, a method of installing an elastomeric component on a wall includes aligning the retaining feature with the retaining hole adjacent the first side of the wall, inserting a probe into the blind pocket, inserting the insertion end portion into the retaining hole until a contact location on the retention end portion makes first contact with the first edge of the retaining hole, pushing the insertion end portion with the probe and thereby moving the insertion end portion through the retaining hole from the first side to the second side, and engaging the second side of the wall with the catch.

In yet another aspect, an apparatus for installing an elastomeric component on a wall includes a fixture configured to hold a wall and a probe moveable relative to the fixture. The wall has first and second sides and a retaining hole extending between the first and second sides. The probe is configured to be inserted into a blind pocket of a retaining feature and move a retention end portion of the retaining feature through the retaining hole and into engagement with the wall.

The various aspects and embodiments provide significant advantages relative to the prior assemblies and methods. For example, in one embodiment, the installation of the elastomeric component may be accomplished entirely from one side of the wall solely through a pushing action, which mimics a pulling action as the retention portion stretches and thins during insertion, rather than compressing and thickening. As such, access to the far side of the wall is not required. The installation may be performed manually, for example by grasping and manipulating a probe, semi-automatically or automatically. The assembly provides a clean appearance, without a residual leading tag.

BRIEF DESCRIPTION OF THE DRAWINGS

The Figures show different embodiments of the assembly, system and apparatus and methods for use and assembly thereof.

FIG. is end view of the components shown in FIG. 4.

DETAILED DESCRIPTION OF THE DRAWINGS

It should be understood that the term "plurality," as used herein, means two or more. The term "longitudinal," as used herein means of or relating to length or the lengthwise direction 2, for example a direction running along the axis 6 of a retaining hole 16 of a wall 10 and/or retaining feature of an elastomeric component 14. The term "lateral," as used herein, means situated on, directed toward or running in a direction 4 orthogonal to the longitudinal direction 2, for example in the plane of body feature 8 of elastomeric component 14. The term "coupled" means connected to or engaged with, whether directly or indirectly, for example with an intervening member, and does not require the engagement to be fixed or permanent, although it may be fixed or permanent. For example, the retaining feature 12 may be coupled to the body feature 8 directly or indirectly via a hinge component 52.

The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first direction may be the same as a second direction, with each simply being applicable to different components.

It should be understood that the phrase "rigid wall" refers to a component 10 having a thickness, and which has less flexibility than a corresponding elastomeric component 14 being coupled thereto, such that the elastomeric component will tend to deform rather than deforming the rigid wall, for example by expanding the size of a hole 16 therein. It should be understood that the term "wall" refers to any component having a thickness, regardless of its length, width or shape, and includes a rigid wall.

Figure 9:
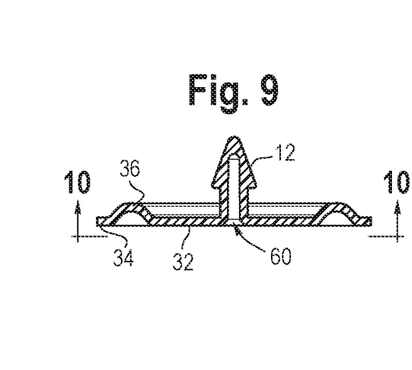
FIG. 9 is a cross-sectional view of another embodiment of an elastomeric component.
Figure 10:
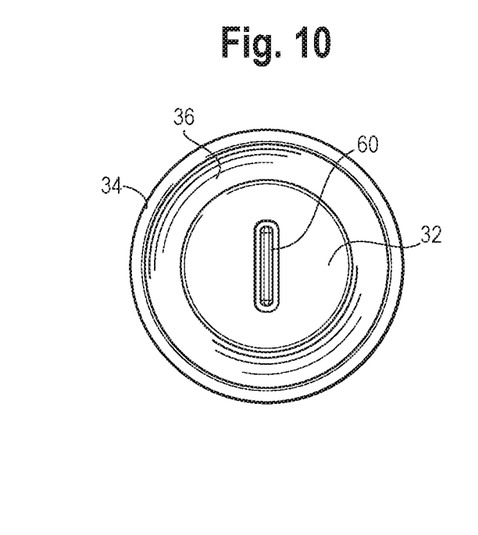
FIG. 10 is a retention end view of the elastomeric component shown in FIG. 9.
Figure 12:
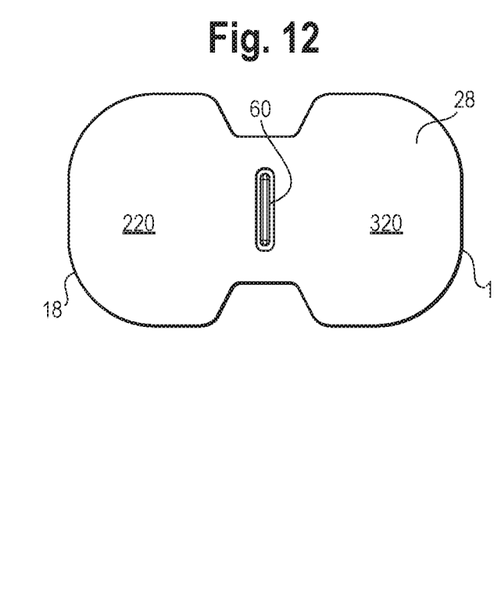
FIG. 12 is a retention end view of an alternative embodiment of an elastomeric component.
Figure 13:
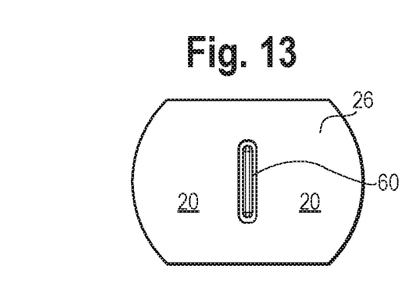
FIG. 13 is a retention end view of an alternative embodiment of the elastomeric component.
Figure 14:
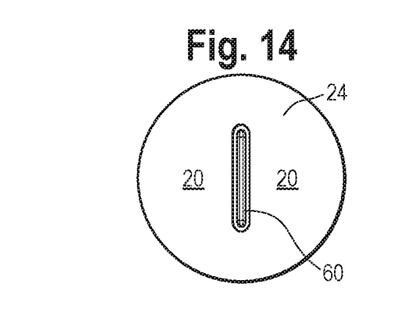
FIG. 14 is a retention end view of an alternative embodiment of an elastomeric component.
Figure 15:
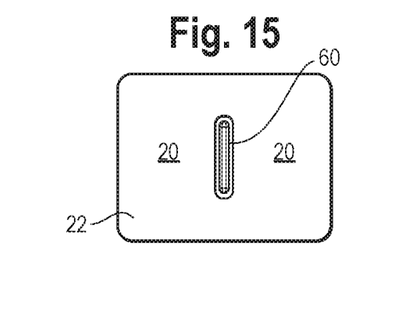
FIG. 15 is a retention end view of an alternative embodiment of an elastomeric component.
Figure 16:
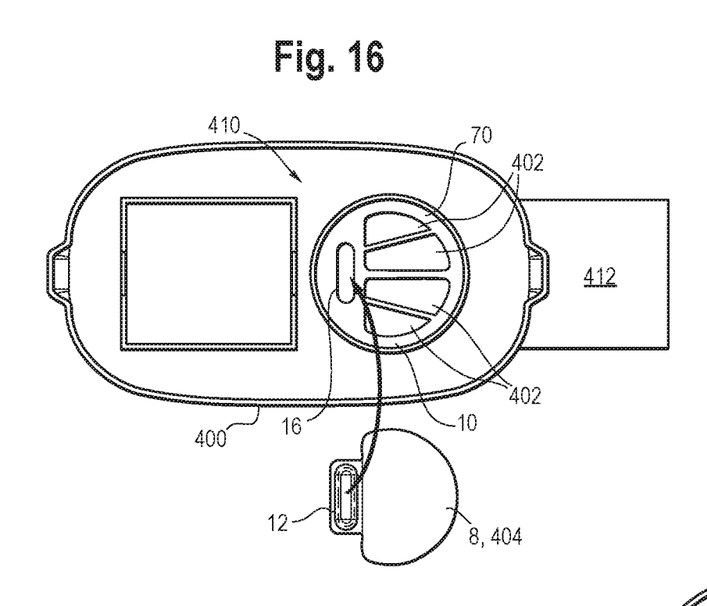
FIG. 16 is a top view of a medical device having a wall and an elastomeric component in a disengaged position.
Figure 17:
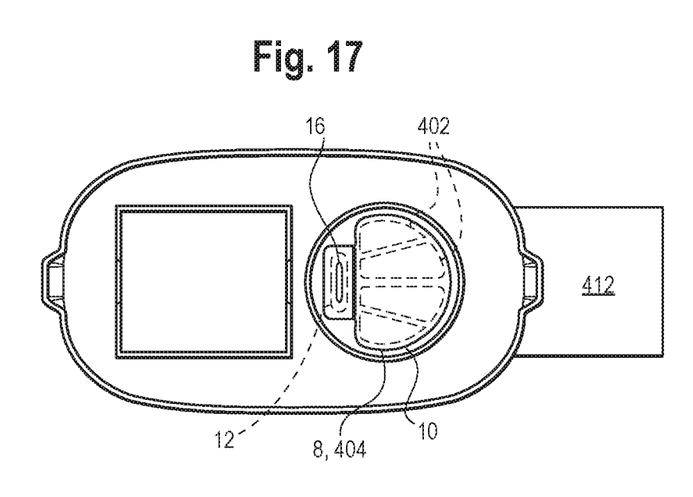
FIG. 17 is a top view of the medical device shown in FIG. 16 with the elastomeric component in a retained position.
Figure 18:
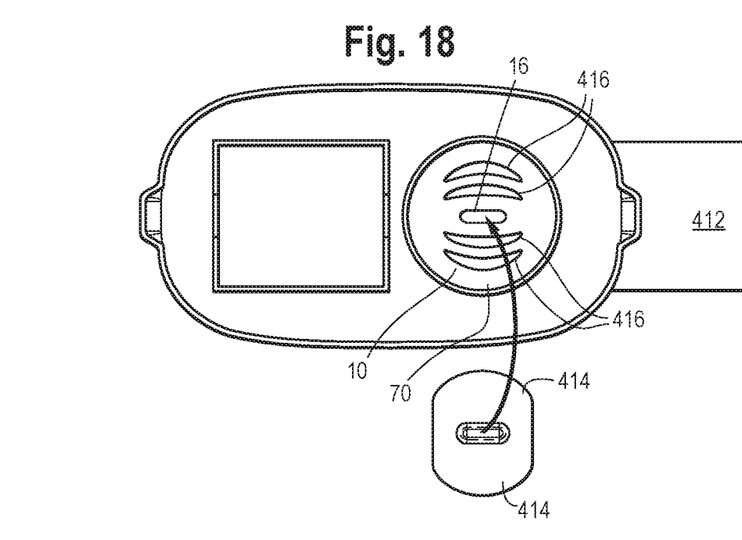
FIG. 18 is a top view of another embodiment of a medical device having a wall and an elastomeric component in a disengaged position.
Figure 19:
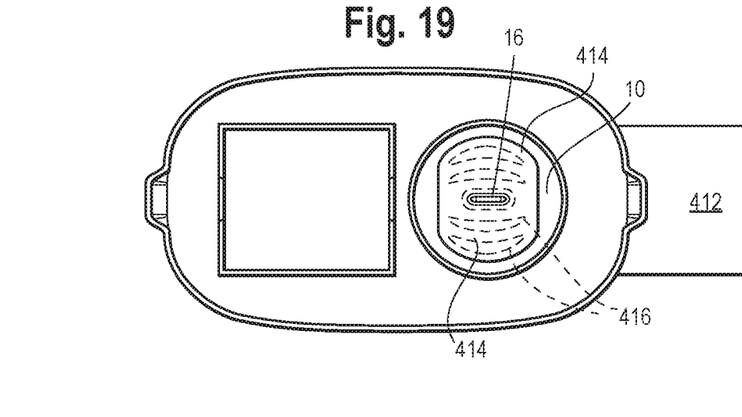
FIG. 19 is a top view of the medical device shown in FIG. 18 with the elastomeric component in a retained position.

Referring to FIGS. 1-15, an elastomeric component 14 includes a body feature 8 and a retaining feature 12. The elastomeric component may be made for example of thermoplastic elastomers (TPE), including without limitation liquid silicone rubber (LSR), silicone, natural rubber, synthetic rubber, or any other soft flexible material that may be molded, cast, die cut or formed into a desired shape. In one embodiment, the body feature 8 is configured as a valve, for example having one or more flaps 20, 220, 320, each with a free end 18. The flaps 20 may define a rectangular (FIG. 15), circular (FIG. 14), or butterfly valves 22, 24, 26, 28 (FIGS. 12, 13). In other embodiments, the body feature may be a circular valve 30 (FIGS. 7, 8) having a moveable circumferential edge or outer periphery 34, or may be formed as a diaphragm valve 32 (FIGS. 9, 10) with an outer periphery 34 and a hinged intermediate portion 36. In yet other embodiments, the elastomeric component, and body feature, may define a grommet, seal, or other known devices. In one embodiment, the body feature 8 is substantially flat and extends within a plane in the lateral direction 4. In other embodiments, the body feature may define a bellow, but extend in a lateral direction 4. In other embodiments, the body feature may be non-planar, and may extend or be formed in various directions and planes. In general, for various medical respiratory devices, the geometry of the various valves is scalable within a wide range of dimensions, including without limitation from 10 millimeters to 100 millimeters.

The retaining feature 12 is coupled to the body feature 8, for example by integrally molding the retaining feature and body feature. The retaining feature may also be coupled to the body feature with mechanical fasteners, adhesives, or intermediate components, such as hinge 52, whether an integral living hinge or a separate lunge component.

The retaining feature 12 includes an insertion end portion 40 and a retention end portion 42 spaced apart from the insertion end portion along the longitudinal axis 6, with a stem 47 extending between the insertion and retention end portions. The insertion end portion 40 has a tapered outer surface 44 extending outwardly from an outermost end 48 to a catch 46, which is spaced apart from the retention end portion 42. Intermediate along the tapered outer surface 44 is a contact location 50, which is the location that first makes contact with an edge of a retaining hole formed in the rigid wall, whether a surface edge, or an inner chamfered surface thereof. The contact location 50 may, in one embodiment, be defined as a peripheral or circumferential line 52 extending around the insertion end portion. The contact location 50, 52 is spaced apart from the catch 46 a first distance Y.

The retaining feature 12 has a blind pocket 60, 160 extending from the retention end portion interiorly of retaining feature, including through the stem 47 and a portion of the insertion end portion, along the longitudinal axis 6. The blind pocket 50 terminates at an end location 62 within the insertion end portion spaced from the catch 46 a second distance X, with X being greater than Y (X>Y). The end location 62 is defined as the location where a probe applies a force to the retaining feature. It should be understood that the contact location 50, 52 may be variably positioned along the outer surface 44 of the insertion end portion 40, depending on the size and shape of the hole 16, but is always positioned below, or on the catch 46 side of the end location 62.

Figure 6:
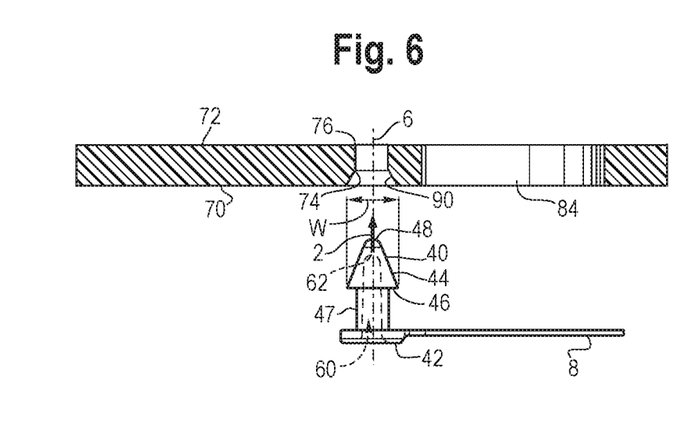
FIG. 6 is a side view of the components shown in FIG. 4.
Figure 7:
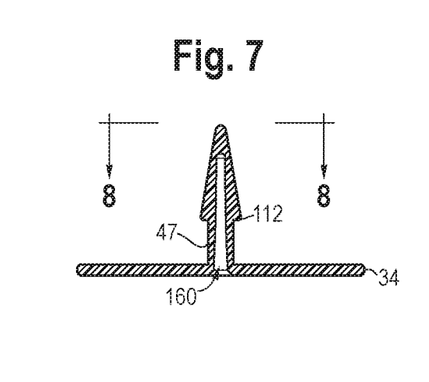
FIG. 7 is a cross-sectional view of another embodiment of an elastomeric component.
Figure 8:
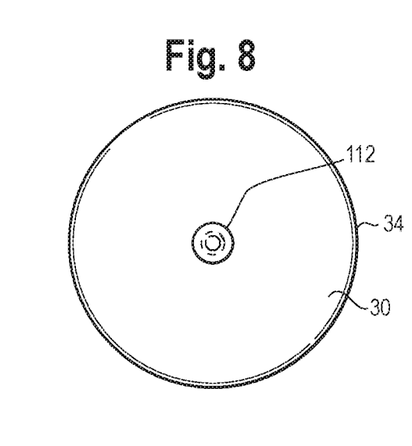
FIG. 8 is a retention end view of the elastomeric component shown in FIG. 7.

In one embodiment, as shown in FIGS. 7 and 8, the retaining feature may be configured as a post 112 having a conical, or frusto-conical, outermost surface 44, with the blind pocket 160 formed as a central hole having an inner diameter. In another embodiment, shown in FIGS. 3-6, the retaining feature 12 may be elongated in one direction orthogonal to the longitudinal axis, so as to have a length L and width W, with L>W. In this embodiment, the blind pocket 60 is correspondingly formed as an elongated slot.

Figure 1:
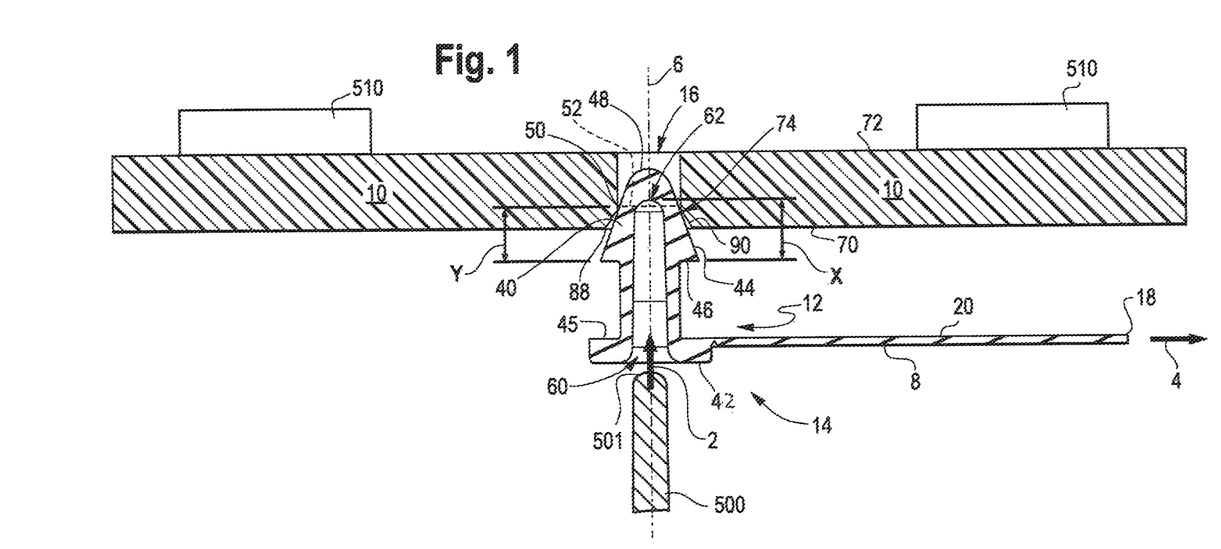
FIG. 1 is a cross-sectional view of an elastomeric component in an insertion position relative to a wall.
Figure 5:
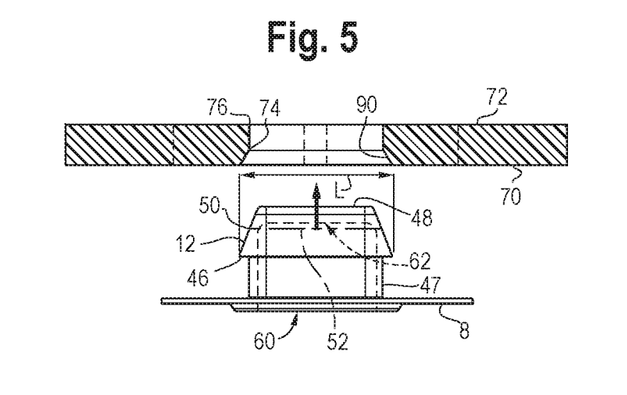
Figure 20:
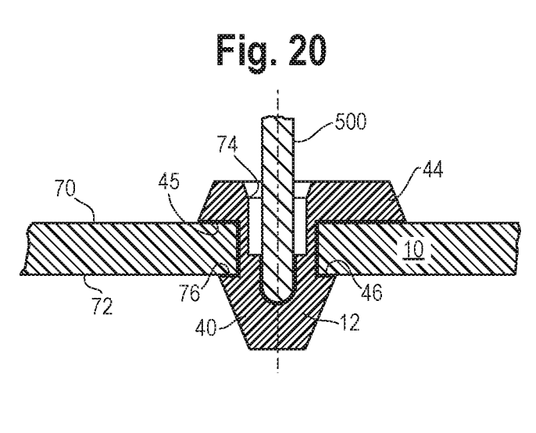
FIG. 20 is a cross-sectional view of a view of another embodiment of an elastomeric component in a retained position relative to a wall.

Referring to FIGS. 1-6 and 11, a wall 10, which may be rigid, has first and second sides 70, 72, with the retaining hole 60 extending between the first and second sides. The wall may be made of plastic, metal, elastomeric materials, composites and other known materials, or combinations thereof. The retaining hole has first and second edges 74, 76 proximate the first and second sides respectively. For example, as shown in FIG. 20, the edges 74, 76 are positioned on the first and second sides at the junction of the hole 16, while in FIG. 6, a the first edge 74 is spaced inwardly from the first side 70, and in FIG. 21 both the first and second edges 74, 76 are spaced inwardly from the first and second sides 70, 72 respectively. A port 80, such as a valve opening, may be positioned adjacent the retaining hole 16. The port 80 may include a cross member 84 which divides the port into a plurality of ports 82. The periphery of the side 70 surrounding the port 80, together with the cross member 84, define a valve seat for the body 8, which defines a valve. As mentioned, one or both of the first and second edges 74, 76 may be formed interiorly from the first and second sides 70, 72, as shown for example in FIGS. 1, 5, 6 and 21, and the first edge 74 may formed at the end of a taper or chamfer 90 on the first side as shown in FIGS. 1, 5 and 6, which extends inwardly from an edge 88. It should be understood that the first edge 74 is the edge that first comes into contact with the contact location 50, 52 on the insertion end portion 12.

Figure 11:
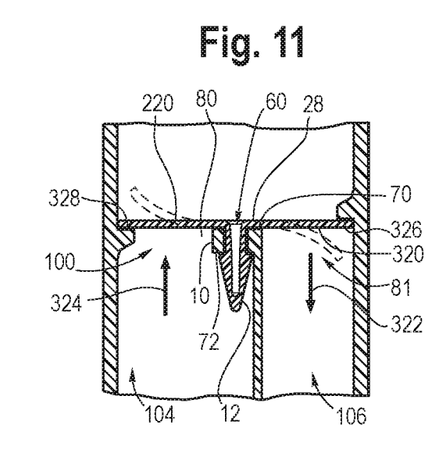
FIG. 11 is a cross-sectional view of another embodiment of an elastomeric component.

As shown in FIG. 11, the rigid wall 10 may include a pair of ports 80, 81, each covered by one of the flaps 220, 320 of a two-way valve, for example a butterfly valve and each opening into separate passageways, for example an inhalation passageway 104 and an exhalation passageway 106. The valve flaps 220, 320 pivot in opposite directions 324, 322 in response to a flow, e.g., due to inhalation or exhalation of a user, with the ends 18 engaging stops 326, 328 such that each flap 220, 230 is configured as a one-way valve. In this embodiment, the wall 10 is configured as a central portion between the passageways 104, 106.

Figure 2:
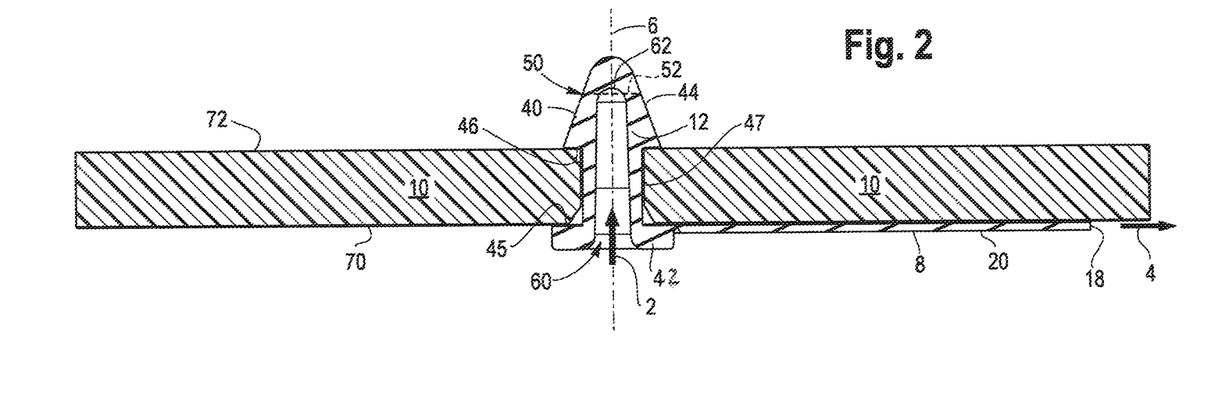
FIG. 2 is a cross-sectional view of the elastomeric component in a retained position relative to a wall.
Figure 3:
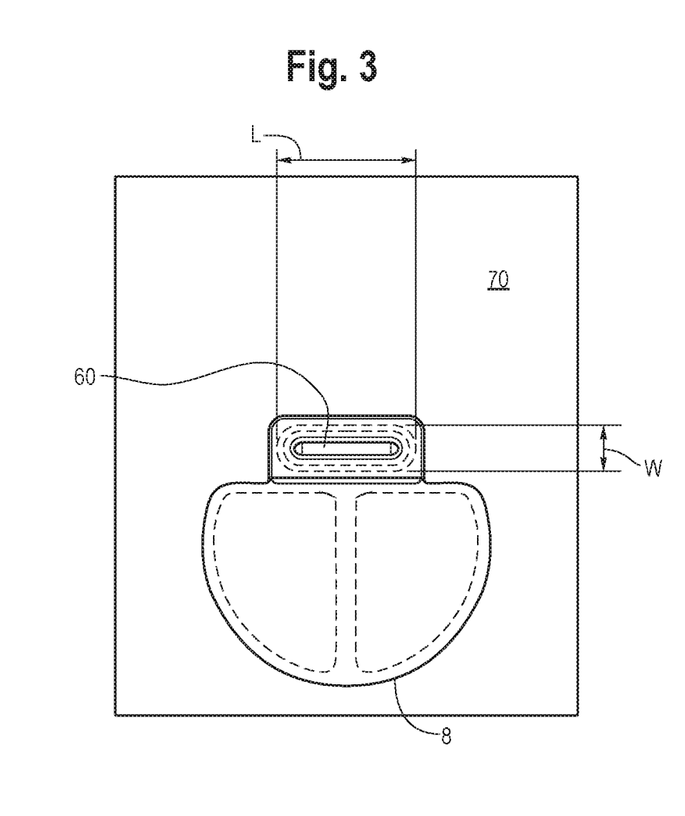
FIG. 3 is a top view of an elastomeric component installed on a wall.
Figure 4:
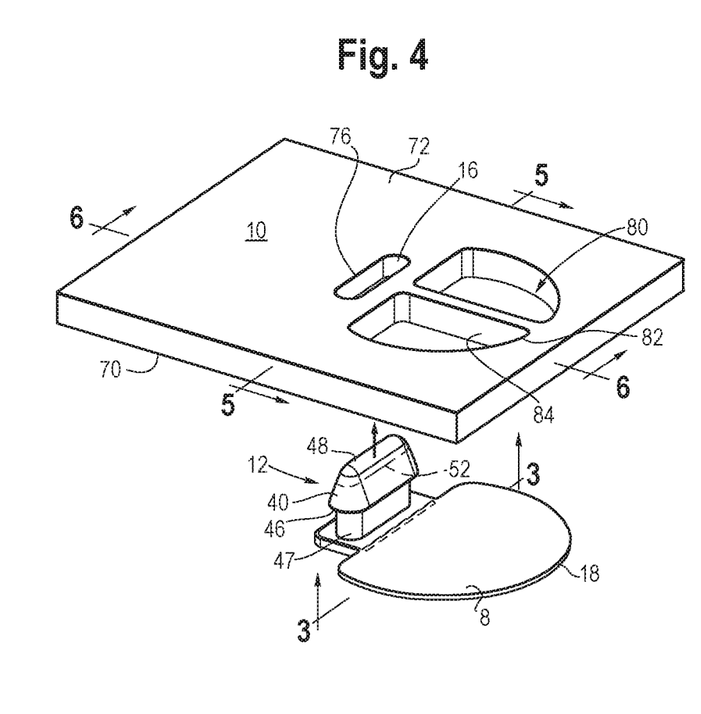
FIG. 4 is an exploded view of the elastomeric component and wall shown in FIG. 3.
Figure 21:
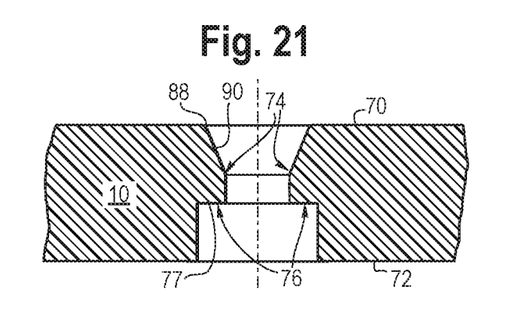
FIG. 21 is a cross-sectional view of another embodiment of a wall.

The insertion end portion 12 is moveable through the retaining hole 16 from the first side 70 to the second side 72 between an insertion position (FIG. 1) and a retained position (FIG. 2). The catch 46 engages the second side 72 of the rigid wall 10 when the insertion end portion is moved to the retained position (FIG. 2), while the contact location 50 of the insertion portion 12 makes a first contact with the first edge 74 of the retaining hole 16 when the insertion end portion is in the insertion position (FIG. 1). Alternatively, the catch 46 may engage a shelf 77, disposed interiorly of the retaining hole 16 at a spaced apart location from the second side as shown in FIG. 21.

In one embodiment, a medical device 400 defines the rigid wall. For example, the medical device may include a respiratory device (FIGS. 16-19), such as an aerosol delivery device, including without limitation a nebulizer, holding chamber, user interfaces such as masks and mouthpieces, ventilator devices and the like, which may interface with a metered dose inhaler (MDI). The respiratory device may include a chamber 410 and a mouthpiece 412. In various embodiments, the rigid wall may have a port or a plurality of ports 402, 416 over which a valve flap 404, or plurality of flaps 414, covers and seals in a normally closed position in the absence of any flow. The opening and closing of the port(s) 402 in the rigid wall 10 allows for the flow of fluid, e.g., liquid or gas, and controls such flow by a differential of pressure.

In operation, a method of installing an elastomeric component on a rigid wall includes aligning the retaining feature 12 with the retaining hole 16 adjacent the first side 70 of the wall 10, as shown in FIG. 1. A probe 500 is inserted into the blind pocket 60. The insertion end portion 40 is inserted into the retaining hole 16 until the contact location 50, 52 on the retention end portion makes first contact with the first edge 72 of the retaining hole 16. The first contact may be point contact, a plurality of point contacts, which may be planar or non-planar, or may include a circumferential contact location, or other configurations.

The probe 500 is then actuated, or moved, in the longitudinal direction 2, pushing the insertion end portion 40 and thereby moving the insertion end portion 40 through the retaining hole 16 from the first side 70 to the second side 72. The pushing of the insertion end portion mimics a pulling action acting on the insertion end portion, due to the relative dimensions of X and Y, such that the insertion end portion 40 stretches and thins, rather than compresses and thickens, as would normally be expected from such pushing action. As the insertion end portion 40 passes through the retaining hole 16, the catch 46 engages the second side 72 of the rigid wall. At the same time, the retention end portion 42, which is also configured with a catch 45, or shoulder, engages the first side 70 of the rigid wall, or an interior shelf, thereby fixing the elastomeric component on the rigid wall. In this way, it should be understood that the first and second sides may include interior shelves, together with the outermost surface. The probe 500 may thereafter be removed by moving the probe in an opposite direction along the longitudinal axis 2. In this way, the installation is completed by a single movement of a single probe 500 on one side of the rigid wall, without any requisite activity on the opposite side thereof.

An apparatus for installing an elastomeric component on a rigid wall includes a fixture 510 configured to hold a rigid wall 10, or medical device, and the probe 500 moveable relative to the fixture. The probe 500 is shaped to be received in the blind pocket 60, 160, and may be elongated in a lateral direction (i.e., have a width) or may be configured with a cylindrical outer surface, depending on the shape of the blind pocket. The end 501 of the probe may be rounded so as to not penetrate into, or poke through, the insertion feature.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An elastomeric component kit comprising:
a body feature;
a retaining feature coupled to the body feature, the retaining feature comprising an insertion end portion, and a retention end portion spaced apart from the insertion end portion along a longitudinal axis, the insertion end portion defining a catch spaced apart from the retention end portion and having a contact location adapted to make first contact with an edge of a retaining hole, wherein the contact location is spaced apart from the catch a first distance, and wherein the retaining feature has a blind pocket extending from the retention end portion interiorly of the retaining feature along the longitudinal axis, wherein the blind pocket terminates at an end location spaced from the catch a second distance, wherein the second distance is greater than the first distance, and wherein the contact location is positioned between the end location and the catch; and
a probe insertable into the blind pocket and engageable with the end location so as to apply a force to the end location along the longitudinal axis.

2. The elastomeric component kit of claim 1 wherein the body feature comprises a valve member.

3. The elastomeric component kit of claim 1 wherein the body feature and retaining feature are integrally molded as a single component.

4. An assembly of a wall and an elastomeric component comprising:
the wall having first and second sides and a retaining hole extending between the first and second sides, the retaining hole having first and second edges proximate the first and second sides respectively; and
the elastomeric component comprising;
a body feature; and
a retaining feature coupled to the body feature, the retaining feature comprising an insertion end portion and a retention end portion spaced apart from the insertion end portion along a longitudinal axis, wherein the insertion end portion is moveable through the retaining hole from the first side to the second side between an insertion position and a retained position, wherein the insertion end portion defines a catch spaced apart from the retention end portion, wherein the catch engages the second side of the will when the insertion end portion is moved to the retained position, and wherein the insertion end portion has a contact location making a first contact with the first edge of the retaining hole when the insertion end portion is in the insertion position, wherein the contact location is spaced apart from the catch a first distance, and wherein the retaining feature has a blind pocket extending from the retention end portion interiorly of the retaining feature along the longitudinal axis, wherein the blind pocket terminates at an end location spaced from the catch a second distance, wherein the second distance is greater than the first distance, and wherein the contact location is positioned between the end location and the catch; and
a probe insertable into the blind pocket and engageable with the end location so as to apply a force to the end location along the longitudinal axis.

5. The assembly of claim 4 wherein the body feature comprises a valve member.

6. The assembly of claim 4 comprising a medical device defining the wall.

7. The assembly of claim 6 wherein the medical device comprises a holding chamber.

8. The assembly of claim 7 wherein the holding chamber comprises a user interface portion defining the wall.

9. A method of installing an elastomeric component on a wall comprising:
providing the wall having first and second sides and a retaining hole extending between the first and second sides, the retaining hole having first and second edges proximate the first and second sides respectively;
providing the elastomeric component comprising;
a body feature; and
a retaining feature coupled to the body feature, the retaining feature comprising an insertion end portion and a retention end portion spaced apart from the insertion end portion along a longitudinal axis, wherein the insertion end portion defines a catch spaced apart from the retention end portion, and wherein the retaining feature has a blind pocket extending from the retention end portion interiorly of the retaining feature along the longitudinal axis;
aligning the retaining feature with the retaining hole adjacent the first side of the wall;
inserting the insertion end portion into the retaining hole until a contact location on the retention end portion makes first contact with the first edge of the retaining hole, wherein the contact location is spaced apart from the catch a first distance, and wherein the blind pocket terminates at an end location spaced from the catch a second distance, wherein the second distance is greater than the first distance, and wherein the contact location is positioned between the end location and the catch;
inserting a probe into the blind pocket and engaging the end location of the blind pocket;
pushing the insertion end portion with the probe along the longitudinal axis and thereby moving the insertion end portion through the retaining hole from the first side to the second side; and
engaging the second side of the wall with the catch.

10. The method of claim 9 wherein the body feature comprises a valve member.

11. The method of claim 10 comprising a medical device defining the wall.

12. The method of claim 11 wherein the medical device comprises a holding chamber.

13. The method of claim 12 wherein the holding chamber comprises a user interface portion defining the wall.

14. The method of claim 9 further comprising engaging the first side of the wall with the retention end portion.

15. The method of claim 14 wherein the retention end portion comprises a second catch engaging the first side of the wall.

* * * * *